United States Patent
Rubio

(10) Patent No.: US 6,226,817 B1
(45) Date of Patent: May 8, 2001

(54) PILLOW CONSTRUCTION

(76) Inventor: Horacio C. Rubio, 4664 FM 1889, Robstown, TX (US) 78380

( * ) Notice: Subject to any disclaimer, the term of this patent is extended or adjusted under 35 U.S.C. 154(b) by 0 days.

(21) Appl. No.: 09/680,062

(22) Filed: Oct. 4, 2000

(51) Int. Cl.[7] .......................... A47C 27/15; A47C 27/14; A61G 9/00
(52) U.S. Cl. .................................... 5/632; 5/636
(58) Field of Search ............... 5/632, 636, 630, 5/633, 646

(56) References Cited

U.S. PATENT DOCUMENTS

| | | | |
|---|---|---|---|
| 2,700,779 | * 2/1955 | Tolkowsky | 5/632 |
| 3,648,308 | 3/1972 | Greenawalt | 5/632 |
| 4,850,067 | 7/1989 | Latorre | 5/436 |
| 4,850,068 | 7/1989 | Waldin | 5/431 |
| 4,853,993 | 8/1989 | Walpin | 5/636 |
| 4,918,774 | 4/1990 | Popitz . | |
| 5,479,667 | 1/1996 | Nelson | 5/632 |
| 5,581,831 | 12/1996 | Xiang | 5/636 |
| 5,797,154 | 8/1998 | Contreras | 5/636 |
| 5,987,675 | * 11/1999 | Kim | 5/632 |
| 6,003,177 | 12/1999 | Ferris | 5/636 |
| 6,006,381 | 12/1999 | Tandrup | 5/637 |
| 6,052,849 | 4/2000 | Dixon | 5/643 |

* cited by examiner

Primary Examiner—Alexander Grosz
(74) Attorney, Agent, or Firm—G. Turner Moller

(57) ABSTRACT

A pillow construction of complex shape is designed to alleviate the symptoms of acid reflux. The pillow comprises a central wedge shaped ramp on which the torso of the user is supported when lying on the back and a head support section. The head support section provides a substantial bulge immediately adjacent the ramp to support the user's head when lying on the back and lower areas on each side thereof to support the user's head when lying on one side. The ramp and head support section together provide a generally T-shaped outline. On each side of the ramp is a lower flat section providing a recess for receiving and supporting the user's shoulder.

7 Claims, 2 Drawing Sheets

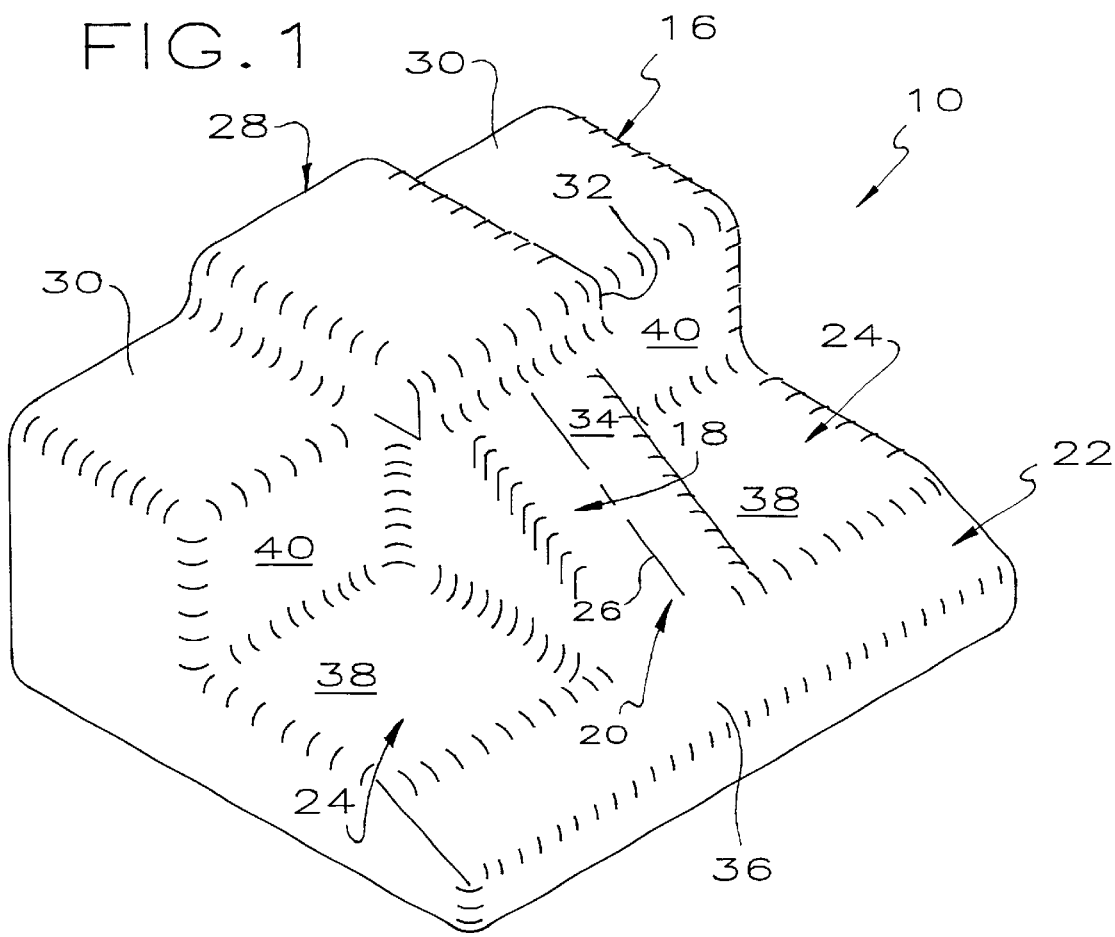
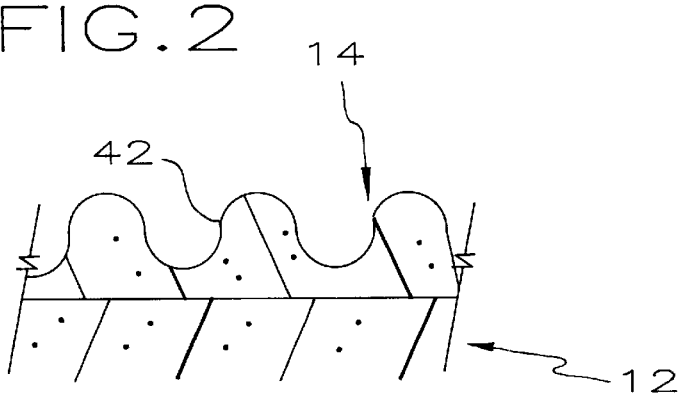

PILLOW CONSTRUCTION

BACKGROUND OF THE INVENTION

There are many disclosures of pillows in the prior art, all of which are aimed at providing an aid to deep, prolonged, satisfying sleep. Although there are many sleep disorders or conditions that hinder satisfying sleep, one category is known by the common name of reflux or acid reflux which is a simplification of the term gastroesophageal or laryngopharyngeal reflux. Basically, stomach contents are periodically belched upwardly into the esophagus, leaving an uncomfortable or burning sensation behind the breast bone, as high as at the base of the throat or even up to the mouth. Acid reflux occurs in a wide spectrum of symptoms, the more acute of which hinder or prevent satisfying sleep.

Although drugs are available to treat persistent acid reflux, one of the first suggested treatments is to elevate the head during sleep. It is not sufficient simply to put two pillows under the person's head. Both the head and thorax of the person must be elevated with any hope of alleviating the symptoms of acid reflux. But, properly done, this simple approach is effective, to a greater or lesser extent, with a large number of people suffering from acid reflux. It is accordingly not surprising that a number of pillow constructions have been proposed to aid in overcoming the symptoms of acid reflux and thereby promote deep, prolonged, satisfying sleep. It is this type device to which this invention most nearly relates.

Disclosures relevant to the disclosure of this invention are found in U.S. Pat. Nos. 3,648,308; 4,850,067; 4,850,068; 4,853,993; 4,918,774; 5,479,667; 5,581,831; 5,797,154; 6,003,177; 6,006,381 and 6,052,849.

SUMMARY OF THE INVENTION

In this invention, a pillow of complex shape is provided. A central part of the pillow is designed to elevate the user's head and thorax while supporting the user's back when the person lies supine on the pillow. Lateral portions of the pillow are designed to support the user's head and shoulder when the user turns on one side.

To these ends, a central section of the pillow provides a wedge shaped ramp leading upwardly to a head support assembly. The head support assembly includes a central bulge adjacent the ramp for supporting the user's head when lying supine on the ramp for elevating the head and minimizing or eliminating any acid reflux reaching the mouth. The head support assembly extends laterally of the ramp and provides a pair of laterally extending wings, below the bulge, for supporting the user's head when lying on one side or the other. The pillow also provides a shoulder support section on each side of the ramp for supporting the shoulder of a user when the person lies on one side.

It is an object of this invention to provide an improved pillow.

It is an object of this invention to provide a pillow of complex configuration for supporting a person during sleep to minimize the symptoms of acid reflux.

A further object of this invention is to provide a pillow having a central ramp for elevating the upper thorax and head of a person lying supine on the pillow.

Another object of this invention is to provide a pillow having shoulder support sections laterally from a central ramp.

These and other objects and advantages of this invention will become more apparent as this description proceeds, reference being made to the accompanying drawings and appended claims.

BRIEF DESCRIPTION OF THE DRAWINGS

FIG. 1 is an isometric view of one embodiment of the pillow of this invention;

FIG. 2 is an isometric view of a foam core of the pillow of FIG. 1;

DETAILED DESCRIPTION

Figure 3:
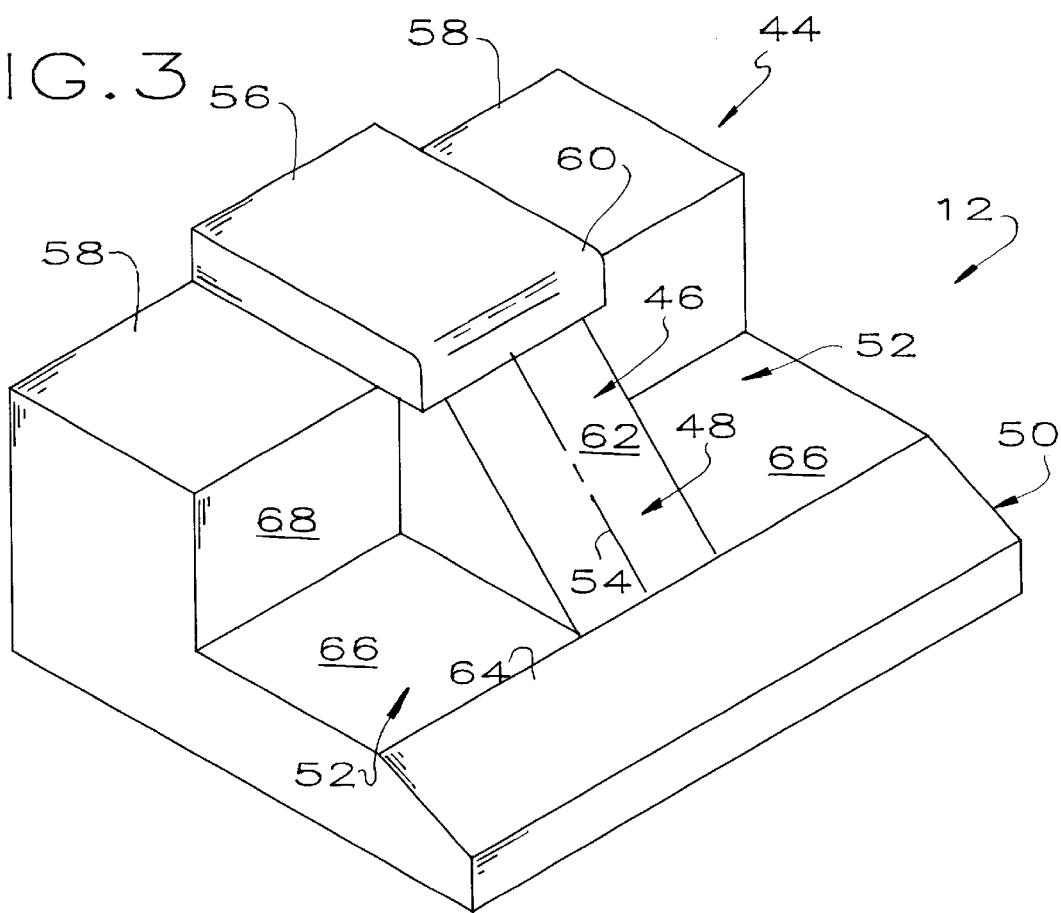
FIG. 3 is a front view of the foam core of FIG. 2.

Referring to FIGS. 1–4, one embodiment of a pillow 10 of this invention comprises a core 12 and a foam covering 14.

The core 12 is made of a relatively soft foam material and is of complex configuration providing the basic shape of the pillow 10. The foam covering 14 acts to provide a desirable surface texture and obscures defects, if any, in the core 12. When manufacturing small numbers of pillows 10 of this invention, it is desirable to provide a separate core 12 and foam covering 14 because the core 12 can be made by starting with a block of foam material, cutting away parts that are not needed and gluing blocks of core foam material onto the carcass to provide increased material where needed, e.g. under the user's head.

Although the pillow 10 is illustrated as comprising a core 12 and a separate covering 14, when larger production runs make it economic, it is contemplated to provide a mold in which to cast a complete pillow. This reduces the labor content of a finished pillow and provides a more professional appearance in the sense that seams and the like, visible on the back of current models, will not be present.

The pillow 10 comprises a head support section 16, a thoracic support section 18, a lumbar support section 20, a waist support section 22 and a pair of shoulder support sections 24. It will be seen that the pillow 10 is symmetrical about a central plane or axis 26. As will be more fully apparent hereinafter, it will be appreciated that the pillow 10 is a rounded and smoothed version of the more angular core 12 because of the effect of the foam pad 14. In other words, the foam pad 14 not only provides a desirable surface texture, it also modifies the shape of the underlying core 12 to the extent of providing a rounded pillow 10 having smooth, more comfortable edges rather than the angular edges of the core 12. This is, of course, more cosmetic than anything else because the foam material of the core 12 is quite soft and the edges, even though they appear sharp and angular, are of soft foam and are not uncomfortable.

The head support section 16 extends throughout the width of the pillow 10 and comprises a central bulge 28 supporting the person's head when lying supine on the thoracic support section 18 and a pair of laterally spaced wings 30 lower than the bulge 28. The central bulge 28 projects forwardly of the wings 30 and overlies the thoracic support section 18 and acts to elevate the user's head to reduce the possibility of any acid reflux reaching the user's mouth. In the overlying section of the bulge 28, the bulge 28 provides a neck roll 32 so the person's neck is supported by the neck roll 32 when the person lies supine on the thoracic support section 18.

The thoracic support section 18 and the lumbar support section 20 comprise parts of a wedge shaped ramp 34 extending from the waist support section 22 to the head support section 16. Although the ramp 36 may be curvilinear, it is conveniently flat. The waist support section 22 extends throughout the width of the pillow 10 and comprises a broad roll or curved section 36 which supports the back immediately above the hips.

The shoulder support sections 24 comprise recesses or generally flat areas 38 on opposite sides of the ramp 34. The purpose is to provide a place to receive, and a support for, the shoulders of the user when the person rolls over on one side or the other. The shoulder support sections 24 accordingly provide a generally upright front wall 40 providing a recess for receiving the person's shoulder and allowing the person's head to rest on, and be supported by, the wings 30. The generally horizontal sections 38 provide a support for the person's shoulders.

Use of the pillow 10 should now be apparent. When the person lies supine on the ramp 34, the person's head is supported on the bulge 28, the person's neck is supported by the neck roll 32, the person's thorax and lumbar area is supported on the ramp 34 and the person's pelvis abuts the broad roll 36. When the person rolls on one side or the other, the side of the person's head is supported on the wing 30, the wall 40 provides the space to receive the person's shoulder and chest and the horizontal section 38 supports the person's shoulder and side. It will accordingly be seen that the bulge 28 elevates and supports the person's head and neck above the ramp 34 while the lower wings 30 support the person's head at a suitable level relative to the horizontal section 38.

As shown in FIG. 2, the foam pad 14 is preferably of an egg crate type having a large number of upwardly extending mounds or protrusions 42. The foam pad 14 provides a suitable surface texture to the pillow 10, provides a rounded shape for the pillow 10 and also obscures any defects in the underlying core 12.

Figure 4:
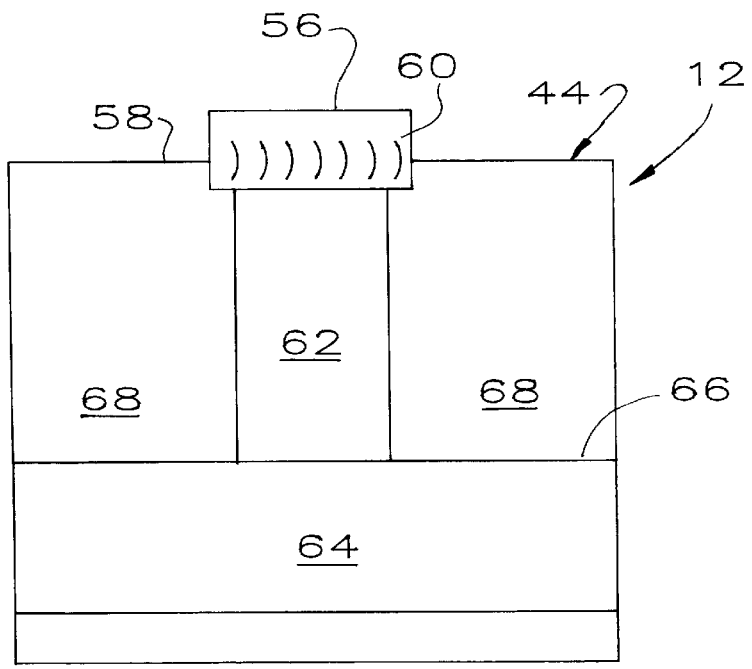
FIG. 4 is an enlarged top view of the pillow of FIG. 1.

The core 12 is best illustrated in FIGS. 3 and 4 and comprises components analogous to those found in the pillow 10. Thus, the core 12 includes a head support section 44, a thoracic support section 46, a lumbar support section 48, a waist support section 50 and a pair of shoulder support sections 52. Similarly, the core 12 is symmetrical about a plane or axis 54. Conveniently, the core 12 is angular because curved edges are more difficult to manufacture and the softness of the foam material prevents any discomfort or objection by the user.

The head support section 44 extends throughout the width of the core 12 and includes a central bulge 56 and a pair of offset wings 58 lower than the bulge 56. The central bulge 56 projects forwardly of the wings 58 and overlies the thoracic support section 46 providing a curved neck roll 60 so the person's neck is supported by the neck roll 60 when the person lies supine on the pillow 10.

The thoracic support section 46 and the lumbar support section 48 comprise parts of a wedge shaped ramp 62 extending from the waist support section 50 to the head support section 44. Although the ramp 62 may be curvilinear, it is conveniently flat. The waist support section 50 extends throughout the width of the core 12 and comprises a beveled section 64 which supports the back immediately above the hips.

The shoulder support sections 52 comprise recesses or generally flat areas 66 on opposite sides of the ramp 62 and a generally upright front wall 68 providing a recess for receiving the person's shoulder and allowing the person's head to rest on, and be supported by, the wings 58. It will accordingly be seen that the depth of the shoulder receiving recesses is sufficient to receive the shoulder and chest of a person for whom the pillow 10 is sized.

Although the pillow 10 may be made of any suitable size, it is preferred to make pillows of a gradation in size, thereby accommodating very large people, small people and people in between.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A pillow designed to support a person's head, neck, shoulder, thorax, lumbar and waist area, comprising a head support assembly to receive and support a person's head and neck connected to a thoracic support assembly which is, in turn, connected to a waist and lumbar support assembly;

the thoracic support assembly comprising a wedge shaped ramp extending from the waist support assembly to a central section of the head support assembly;

the head support assembly extending laterally of the ramp and providing a central elevated bulge above the ramp for supporting the person's head when the person lies supine on the ramp and a pair of wings, lower than the bulge, extending laterally of the bulge for supporting the person's head when the person lies on a side; and a shoulder support assembly, on each side of the ramp, connected to the ramp and to the head support assembly providing a relatively horizontal section for receiving the person's shoulder when the person lies on a side with the person's head on one of the wings.

2. The combination of claim 1 wherein the pillow comprises a foam core having a foam pad bonded to the foam core.

3. The combination of claim 2 wherein the foam core comprises a core thoracic support assembly providing a core wedge shaped ramp; and a core head support assembly providing a core central bulge overlapping the core wedge shaped ramp and a pair of core lateral wings lower than the bulge.

4. The combination of claim 3 wherein that portion of the core central bulge overlapping the core wedge shaped ramp provides a neck roll.

5. The combination of claim 4 wherein the foam pad provides an egg crate exterior.

6. The combination of claim 4 wherein the wings are lower than the ramp.

7. The combination of claim 1 wherein the wings are lower than the ramp.

* * * * *